United States Patent [19]
Goda et al.

[11] Patent Number: 5,939,548
[45] Date of Patent: Aug. 17, 1999

[54] PROCESS FOR PREPARATION OF 3-PIPERAZINYLBENZISOTHIAZOLES

[75] Inventors: Hiroshi Goda; Junichi Sakamoto; Shigeki Sakaue; Sakae Kajihara; Miki Todo, all of Hyogo-ken, Japan

[73] Assignee: Sumitomo Seika Chemicals Co., Ltd., Hyogo, Japan

[21] Appl. No.: 09/128,540

[22] Filed: Aug. 4, 1998

Related U.S. Application Data

[62] Division of application No. 08/938,845, Sep. 26, 1997, Pat. No. 5,861,511.

[30] Foreign Application Priority Data

Oct. 11, 1996 [JP] Japan ............................ 8-269888

[51] Int. Cl.$^6$ ................................................ C07D 417/04
[52] U.S. Cl. ................................................ 544/368
[58] Field of Search ...................................... 544/368

[56] References Cited

U.S. PATENT DOCUMENTS

| | | | |
|---|---|---|---|
| 4,590,196 | 5/1986 | Smith et al. | 514/253 |
| 4,745,117 | 5/1988 | Ishizumi et al. | 514/254 |
| 5,679,827 | 10/1997 | Goda et al. | 558/425 |
| 5,756,806 | 5/1998 | Goda et al. | 558/425 |

FOREIGN PATENT DOCUMENTS

| | | |
|---|---|---|
| 741129 | 11/1996 | European Pat. Off. . |
| 2163432 | 2/1986 | United Kingdom . |

OTHER PUBLICATIONS

HRIB et al., J. Med. Chem. vol.39, pp.4044–4057, 1996.
Bryce, M. R., et al., J. Chem. Soc. Perkin Trans. I, 1(8), 2141–2144 (1988).
Yevich, J. P., et al., J. Med. Chem. 29, 359–369 (1986).
Abstract of JP 63083067 (Apr. 13, 1988).
Abstract of JP 63083085 (Apr. 13, 1988).

*Primary Examiner*—Emily Bernhardt

[57] ABSTRACT

There is disclosed a process for preparing 3-piperazinylbenzisothiazoles comprising reacting the specified 3-halo-1,2-benzisothiazole or 2-cyanobenzenesulfenyl halide in the presence of an alkylene glycol derivative. The process is industrially effective, easy and economical and can provide useful intermediates for production of pharmaceutical preparations.

4 Claims, No Drawings

PROCESS FOR PREPARATION OF 3-PIPERAZINYLBENZISOTHIAZOLES

CROSS-REFERENCE TO RELATED APPLICATION

This is a divisional of application Ser. No. 08/938,845 filed Sep. 26, 1997 now U.S. Pat. No. 5,861,511.

FIELD OF THE INVENTION

The present invention relates to a novel process for preparing 3-piperazinylbenzisothiazoles which are useful compounds as an intermediate for production of pharmaceutical preparations.

BACKGROUND OF THE INVENTION

For preparing 3-piperazinylbenzisothiazole derivatives, mainly two processes have been hitherto known. One of them is a process by reacting 3-halo-1,2-benzisothiazole with a piperazine compound according to the following reaction scheme (1):

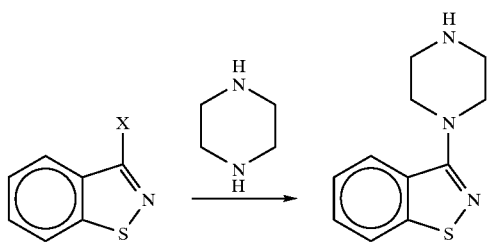

(JP-A 63-83067; JP-A 63-83085; EP-A 196096; J. Chem. Soc., Perkin. Trans., 1(8), 2141. 1988; Ger. Offen., 3530089; J. Med. Chem., 29(3), 359, 1986), and the other one is a process which is disclosed in JP-A 8-291134 which was previously filed by the present applicant, according to the reaction scheme (2):

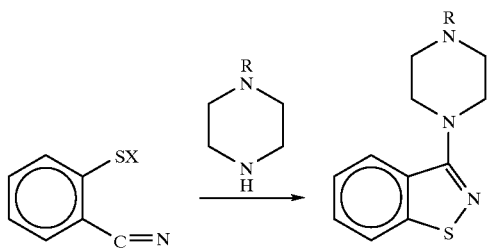

wherein X represents Cl or Br, and R represents H, alkyl group having 1 to 6 carbon atoms or substituted alkylene group having 1 to 6 carbon atoms.

OBJECTS OF THE INVENTION

However, the above known techniques require a largely excessive amount of piperazine and very long reaction time and leads to low yield and, thus, they can not be said to be industrially effective processes.

Like this, it was difficult to industrially effectively prepare 3-piperazinylbenzisothiazoles by any known process.

Accordingly, the object of the present invention is to provide an industrially effective process for preparing 3-piperazinylbenzisothiazoles.

This object as well as other objects and advantages of the present invention will become apparent to those skilled in the art from the following description.

SUMMARY OF THE INVENTION

In view of the above circumstances, the present inventors studied intensively in order to provide an easy process for economically effectively preparing 3-piperazinylbenzisothiazoles. As a result, we found that, in a reaction for preparing 3-piperazinylbenzisothiazoles by reacting 3-halo-1,2-benzisothiazole or 2-cyanobenzenesulfenyl halide with a piperazine compound, when the reaction is performed in the presence of an alkylene glycol derivative, the advantages such as reduction in an amount of piperazine to be used, improvement in yield and reduction in reaction time can be shown.

Mechanism therefor is not clear but this may be because the alkylene glycol derivative manifests the phase transfer catalyst-like activity and enhances the solubility of the piperazine compound in a reaction system.

That is, the present invention was done based on such new findings and provides an economically effective process for preparing 3-piperazinylbenzisothiazoles represented by the general formula (IV):

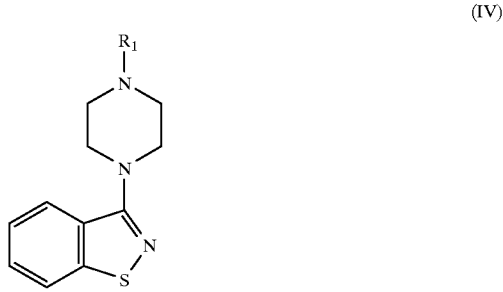

(IV)

wherein $R_1$ represents hydrogen, or alkyl group or substituted alkylene group each having 1–6 carbon atoms, which comprises:

reacting 3-halo-1,2-benzisothiazole represented by the general formula (I):

(I)

wherein X represents Cl or Br, or 2-cyanobenzenesulfenyl halide represented by the general formula (V):

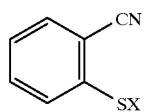

(V)

wherein X is as defined above, with a piperazine compound represented by the general formula (II):

(II)

wherein $R_1$ is as defined above, in the presence of an alkylene glycol derivative represented by the general formula (III):

(III)

wherein $R_2$ and $R_3$ each represent hydrogen, or linear or branched alkyl group having 1 to 4 carbon atoms, and n represents 2–4.

DETAILED DESCRIPTION OF THE INVENTION

The present invention will be explained in detail below.

The 3-halo-1,2-benzisothiazole used in the present invention is represented by the general formula (I) and embodiments thereof are 3-chloro-1,2-benzisothiazole, 3-bromo-1,2-benzisothiazole and the like.

The 2-cyanobenzenesulfenyl halide compound which can be used in the present invention in addition to the above 3-halo-1,2-benzisothiazole is represented by the general formula (V) and can be easily obtained by halogenating a 2-cyanophenylthio derivative according to a process described in JP-A 8-291134 which was filed by the present applicant, and embodiments thereof are 2-cyanobenzenesulfenyl chloride, 2-cyanobenzenesulfenyl bromide and the like.

The piperazine compound used in the present invention is represented by the general formula (II) and examples thereof are piperazine, 1-alkyl-piperazines such as 1-methyl-piperazine, 1-ethyl-piperazine, 1-n-butyl-piperazine and the like, 1-substituted alkylene-piperazines such as 1-imidobutylene-piperazine, 1-amidobutylene-piperazine, 1-((5-indole)ethylene)-piperazine and the like. Particularly, piperazine is preferably used.

An amount of the piperazine compound to be used is in a range of 1 to 10 moles, preferably 2 to 4 moles relative to 1 mole of 3-halo-1,2-benzisothiazole represented by the general formula (I) or 2-cyanobenzenesulfenyl halide represented by the general formula (V).

Further, the alkylene glycol derivative used in the present invention is represented by the general formula (III) and examples thereof are ethylene glycol, propylene glycol, ethylene glycol monomethyl ether, ethylene glycol monoethyl ether and the like. Particularly, ethylene glycol is preferably used.

An amount of the alkylene glycol derivative to be used is in a range of 0.1 to 10 parts by weight, preferably 0.5 to 5 parts by weight relative to 1 part by weight of 3-halo-1,2-benzisothiazole represented by the general formula (I) or 2-cyanobenzenesulfenyl halide represented by the general formula (V).

When the amount of the alkylene glycol derivative to be used is below this range, its effect is not manifested and, when the amount exceeds this range, its effect is no longer manifested, conversely leading to disadvantages on reaction operations.

3-Piperazinylbenzisothiazoles which are an end product in the present invention are represented by the general formula (IV) and embodiments thereof are 3-(1-piperazinyl)-1,2-benzisothiazole, 3-(4-ethyl-1-piperazinyl)-1,2-benzisothiazole, 3-(4-n-butyl-1-piperazinyl)-1,2-benzisothiazole, 3-(4-cyclohexyl-1-piperazinyl)-1,2-benzisothiazole and the like. Alternatively, these compounds may be isolated as a salt of a mineral acid such as hydrochloride and sulfate under the acidic conditions in the presence of hydrochloric acid, sulfuric acid or the like.

A reaction temperature in the process for preparing 3-piperazinylbenzisothiazoles as described is normally in a range of about 70 to about 150° C., preferably about 100 to about 130 ° C. When the reaction temperature is lower than 70° C., the reaction rate becomes slow. On the other hand, when the reaction temperature is higher than 150° C., the side reaction occurs, causing reduction in yield.

A solvent is not necessarily required for a reaction and a non-solvent reaction is preferably used although the reaction may be performed in a solvent. In this case, examples of the solvent to be used are hydrocarbons such as cyclohexane and heptane, aromatic hydrocarbons such as benzene, toluene, xylene, chlorobenzene, dichlorobenzene and trichlorobenzene, polar solvents such as N,N-dimethylformamide and dimethyl sulfoxide. Normally, the amount of them to be used is, but not limited to, 0.1 to 10 parts by weight relative to 1 part by weight of 3-halo-1,2-benzisothiazole represented by the general formula (I) or 2-cyanobenzenesulfenyl halide represented by the general formula (V).

The thus obtained 3-piperazinylbenzisothiazoles represented by the general formula (IV) may be easily isolated and purified from the reaction mixture according to a conventional method such as crystallization or the like.

Surprisingly, by using the process of the present invention, 3-piperazinylbenzisothiazoles which are an end product can be obtained in about ½ to 1/12 reaction time, at about ½ to ⅙ amount of the piperazine compound, and a higher yield by about 20% to 50% as compared with the previous processes.

EXAMPLE

The following Examples further illustrate the present invention but are not to be construed to limit the scope thereof.

Example 1

215.4 g (2.50 mol) of piperazine, 50.0 g of chlorobenzene, 100.0 g of ethylene glycol were placed in a four-neck 1000 ml flask equipped with a stirrer, a thermometer, a dropping funnel and a condenser, 169.5 g (1.00 mol) of 3-chloro-1, 2-benzisothiazole was added dropwise in the melted state at about 120° C. over 1 hour while stirring, which was thereafter stirred for 2 hours to complete the reaction. After excess piperazine was removed with water, the reaction mixture was made acidic with hydrochloric acid, extracted into an aqueous layer, which was made alkaline with aqueous sodium hydroxide to obtain 202.4 g (m.p. 89–90° C.) of 3-(1-piperazinyl)-1,2-benzisothiazole as crystals. Yield from 3-chloro-1,2-benzisothiazole was 92.4%.

Example 2

215.4 g (2.50 mol) of piperazine, 50.0 g of chlorobenzene, 100.0 g of ethylene glycol were placed in a four-neck 1000 ml flask equipped with a stirrer, a thermometer, a dropping funnel and a condenser, 214.1 g (1.00 mol) of 2-cyanobenzenesulfenyl chloride was added dropwise in the melted state at about 120° C. over 1 hour while stirring, which was thereafter stirred for 2 hours to complete the reaction. After excess piperazine was removed with water, the reaction mixture was made acidic with hydrochloric acid, extracted into an aqueous layer, which was made alkaline with aqueous sodium hydroxide to obtain 199.5 g (m.p. 89–90° C.) of 3-(1-piperazinyl)-1,2-benzisothiazole as crystals. Yield from 2-cyanobenzenesulfenyl chloride was 91.1%.

Comparative Example 1

304.2 g (3.53 mol) of piperazine, 7.5 g of chlorobenzene, 39.8 g (0.235 mol) of 3-chloro-1,2-benzisothiazole were placed in a four-neck 1000 ml flask equipped with a stirrer, a thermometer, a dropping funnel and a condenser, which was heated to stir at about 120° C. for 20 hours. After excess piperazine was removed with water, the reaction mixture was made acidic with hydrochloric acid, extracted into an aqueous layer, which was made alkaline with aqueous sodium hydroxide to obtain 24.4 g (m.p. 89 to 90° C.) of 3-(1-piperazinyl)-1,2-benzisothiazole as crystals. Yield from 3-chloro-1,2-benzisothiazole was 47.4%.

Comparative Example 2

86.2 g (1.00 mol) of piperazine and 7.5 g of chlorobenzene were placed in a four-neck 500 ml flask equipped with a stirrer, a thermometer, a dropping funnel and a condenser, 53.5 g (0.25 mol) of 2-cyanobenzenesulfenyl chloride was added dropwise in the melted state at about 130° C. over 1 hour while stirring, which was thereafter stirred for 4 hours to complete the reaction. After excess piperazine was removed with water, the reaction mixture was made acidic with hydrochloric acid, extracted into an aqueous layer, which was made alkaline with aqueous sodium hydroxide to obtain 40.9 g (m.p. 89 to 90° C.) of 3-(1-piperazinyl)-1,2-benzisothiazole as crystals. Yield from 2-cyanobenzenesulfenyl chloride was 74.7%.

What is claimed is:

1. A process for preparing 3-piperazinylbenzisothiazoles represented by the general formula (IV):

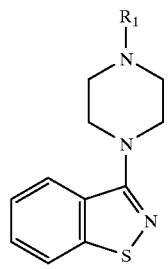

(IV)

wherein $R_1$ represents hydrogen, or alkyl group having 1 to 6 carbon atoms, which comprises:

reacting 3-halo-1,2-benzisothiazole represented by the general formula (I):

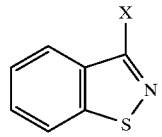

(I)

wherein X represents Cl or Br, with a piperazine compound represented by the general formula (II):

(II)

wherein $R_1$ is as defined above, in the presence of an alkylene glycol derivative represented by the general formula (III):

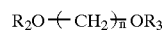

(III)

$$R_2O{+}CH_2{\rightarrow}_n OR_3$$

wherein $R_2$ and $R_3$ each represent hydrogen, or linear or branched alkyl group having 1 to 4 carbon atoms, and n represents 2 to 4.

2. The process according to claim 1, wherein the piperazine compound represented by the general formula (II) is piperazine.

3. The process according to claim 1, wherein 3-piperazinylbenzisothiazole represented by the general formula (IV) is 3-(1-piperazinyl)-1,2-benzisothiazole.

4. The process according to claim 1, wherein the alkylene glycol derivative represented by the general formula (III) is ethylene glycol.

* * * * *